United States Patent
Guiu et al.

(10) Patent No.: US 10,064,883 B2
(45) Date of Patent: Sep. 4, 2018

(54) LIPIODOL-BASED ANTI-TUMOUR EMULSION FOR TREATING CANCER

(71) Applicants: CHU DE DIJON, Dijon (FR); UNIVERSITE DE BOURGOGNE, Dijon (FR)

(72) Inventors: Boris Guiu, Daix (FR); Mathieu Boulin, Dijon (FR); Jean-Pierre Cercueil, Dijon (FR)

(73) Assignee: GUERBET, Villepinte (FR)

( * ) Notice: Subject to any disclaimer, the term of this patent is extended or adjusted under 35 U.S.C. 154(b) by 206 days.

(21) Appl. No.: 14/413,132

(22) PCT Filed: Jul. 5, 2013

(86) PCT No.: PCT/FR2013/051616
§ 371 (c)(1),
(2) Date: May 19, 2015

(87) PCT Pub. No.: WO2014/006349
PCT Pub. Date: Jan. 9, 2014

(65) Prior Publication Data
US 2015/0265640 A1  Sep. 24, 2015

(30) Foreign Application Priority Data

Jul. 6, 2012 (FR) ..................... 12 56556
Jul. 5, 2013 (FR) ..................... 13 56666

(51) Int. Cl.
*A61K 31/704* (2006.01)
*A61K 31/167* (2006.01)
*A61K 31/23* (2006.01)
*A61K 9/00* (2006.01)
*A61K 47/36* (2006.01)
*A61K 9/107* (2006.01)
*A61K 47/44* (2017.01)

(52) U.S. Cl.
CPC .......... *A61K 31/704* (2013.01); *A61K 9/0019* (2013.01); *A61K 9/107* (2013.01); *A61K 31/167* (2013.01); *A61K 31/23* (2013.01); *A61K 47/36* (2013.01); *A61K 47/44* (2013.01)

(58) Field of Classification Search
CPC ..... A61K 31/00; A61K 31/167; A61K 31/704
USPC ................................... 514/34, 620
See application file for complete search history.

(56) References Cited

FOREIGN PATENT DOCUMENTS

WO        2004/075904 A1    9/2004
WO   WO 2009/153346 A2 * 12/2009  ............. A61K 9/16
WO        2012004007 A1    1/2012

OTHER PUBLICATIONS

Takayasu et al, Gan to Kagaku Ryoho 1988, Aug. 15 (8 Pt. 2), 2562-67; English abstract, p. 1.*
Nagamitsu et al, Eur. J. Cancer, 1998, 34(11), 1764-69.*
Favoulet et al, Anti-Cancer Drugs, 2001, 12, 801-806.*
Patrick Favoulet et al; Increased cytotoxicity and stability of Lipiodol-pirarubicin emulsion compared to classical doxorubicin-Lipiodol: Potential Advantage for Chemoembolization of Unresectable Hepatocellular Carcinoma; XP009164708; Anti-Cancer Drugs, vol. 12, Nov. 2001, pp. 803-804.
Yamasaki Takahiro et al; Effect of Transcatheter Arterial Infusion Chemotherapy Using Iodized Oil and Degradable Starch Microspheres for Hepatocellular Carcinoma; Journal of Gastroenterology; vol. 47, No. 6, Jun. 2012, pp. 715-722, XP002687270.
A. Nagamitsu et al.; Targeted Cancer Chemotherapy for VX2 Tumour Implanted in the Colon with Lipiodol as a Carrier; European Journal of Cancer, Pergmon Press, XP004285128; vol. 34, No. 11, Oct. 1998, pp. 1764-1765.
International Search Report dated Sep. 20, 2013 from corresponding International Patent Application No. PCT/FR2013/051616; 6 pgs.

* cited by examiner

*Primary Examiner* — Ganapathy Krishnan
(74) *Attorney, Agent, or Firm* — Maier & Maier, PLLC

(57) ABSTRACT

The present invention relates to a pharmaceutical composition including Lipiodol and a molecule with anti-tumor activity and secondarily a hydroxyethyl starch. The present invention also relates to the use of the compositions according to the invention for treating cancer. According to one embodiment, the pharmaceutical composition according to the invention has between 0.004% and 0.2% by weight of idarubicin, between 0.38% and 2.25% by weight of hydroxyethyl starch and secondarily between 60% and 68% by weight of Lipiodol, and water for injection (or even physiological saline) in a quantity sufficient (q.s.) for 100%.

15 Claims, No Drawings

LIPIODOL-BASED ANTI-TUMOUR EMULSION FOR TREATING CANCER

FIELD OF THE INVENTION

The present invention relates to a pharmaceutical composition comprising Lipiodol and a molecule with anti-tumour activity and secondarily a hydroxyethyl starch. The present invention also relates to the use of the compositions according to the invention for treating cancer.

PRIOR ART

Chemoembolisation techniques are commonly used in the field of cancer treatment and more particularly for treating liver cancer.

This technique consists of restricting the blood circulation in the tumours so as to induce the necrosis thereof. In the context of liver tumour treatment, this procedure consists of accessing the hepatic artery and more particularly the branch of the hepatic artery supplying the tumour in order to inject a chemoembolisation agent therein, which subsequently obstructs the vessels supplying the tumour.

Lipiodol is one of the commonly used chemoembolisation agents. This agent consists of ethyl esters of iodinated fatty acids of poppy-seed oil. It contains 43 to 53% iodine. It is prepared by saponifying poppy-seed oil which releases fatty acids in the form of soaps which are subsequently iodinated with iodine chloride and finally esterified with ethanol.

Poppy-seed oil is extracted from oilseed poppy seeds (*Papaver somniferum*). The main fatty acids contained in this oil are linoleic acid and linolenic acid.

Lipiodol is also used as a contrast medium in the context of radiological investigations.

Lipiodol is sometimes used in combination with a molecule with anti-tumour activity. Conventionally, the molecule with anti-tumour activity (e.g. Doxorubicin) is emulsified with Lipiodol.

However, these emulsions are relatively unstable in vitro and in vivo and are not suitable for obtaining optimum therapeutic effects.

DESCRIPTION OF THE INVENTION

The present invention particularly relates to pharmaceutical compositions comprising Lipiodol and an agent with anti-tumour activity, the stability whereof is greater than that of the compositions according to the prior art.

The present invention thus particularly relates to a pharmaceutical composition comprising Lipiodol, a molecule with anti-tumour activity and a hydroxyethyl starch.

The present invention also relates to a pharmaceutical composition comprising Lipiodol and Idarubicin.

Indeed, it was observed that the Idarubicin/Lipiodol mixture is suitable for obtaining a stable emulsion compared to other emulsions of Lipiodol/molecule with anti-tumour activity. Moreover, this particular composition has particularly advantageous pharmacokinetics.

Within the scope of the present invention, the term "Lipiodol" is intended to denote all ethyl esters of iodinated fatty acids of poppy-seed oil with an iodine content between 33 and 53% (in grams of iodine per 100 ml of end product).

According to one preferred embodiment, the term "Lipiodol" is intended to denote the products marketed under the name Lipiodol Ultra-Fluide® (Guerbet Laboratories, France) and under the name Ethiodol® by Savage (Melville, N.Y.).

According to one preferred embodiment, said pharmaceutical composition is characterised in that said molecule with anti-tumour activity is chosen from the group including antimetabolites, alkylating agents, topoisomerase inhibitors, anti-tumour antibiotics and mitotic spindle poisons.

According to one more preferred embodiment, said anti-tumour molecule is an intercalating agent, topoisomerase inhibitor.

According to one absolutely preferred embodiment, said intercalating agent, topoisomerase inhibitor is an anthracycline and more preferentially Idarubicin.

The applicants succeeded in demonstrating surprisingly that Idarubicin was particularly effective in the pharmaceutical compositions according to the invention. Indeed, this drug was demonstrated to be the most effective of the anticancer agents in vitro on CHC cells lines: HepG2, SNU-398 and SNU-449.

Those skilled in the art know hydroxyethyl starch which is commonly used as succedaneous vascular filling solutes of plasma.

According to one preferred embodiment, said hydroxyethyl starch has a molecular weight between 100,000 and 250,000 Dalton and even more preferentially between 120,000 and 140,000 Dalton.

According to a further preferred embodiment, said hydroxyethyl starch has a molar substitution ratio between 0.30 and 0.70 and more preferentially between 0.35 and 0.45.

According to one absolutely preferred embodiment, said pharmaceutical composition only comprises Lipiodol, a molecule with anti-tumour activity and a pharmaceutically acceptable solvent.

Of the pharmaceutically acceptable solvents (according to the European Pharmacopoeia), water for injection and physiological saline are particularly preferred.

According to one preferred embodiment, the quantity of said molecule with anti-tumour activity is between 0.002% and 0.4% mass/volume (thus with respect to the total volume of the preparation [1% m/v=1000 mg/100 ml]). According to one more preferred embodiment, the quantity of said molecule with anti-tumour activity is between 0.004% and 0.2% mass/volume (thus with respect to the total volume of the preparation). According to one absolutely preferred embodiment, the quantity of said molecule with anti-tumour activity is between 0.03% and 0.07% mass/volume (thus with respect to the total volume of the preparation).

According to one preferred embodiment, the quantity of hydroxyethyl starch is between 0.19% and 4.5% mass/volume (thus with respect to the total volume of the preparation [1% m/v=1000 mg/100 ml]). According to one more preferred embodiment, the quantity of hydroxyethyl starch is between 0.38% and 2.25% mass/volume (thus with respect to the total volume of the preparation). According to one absolutely preferred embodiment, the quantity of hydroxyethyl starch is between 0.5% and 1.5% mass/volume (thus with respect to the total volume of the preparation).

According to one preferred embodiment, the quantity of Lipiodol is between 40% and 80% mass/volume (thus with respect to the total volume of the preparation [1% m/v=1000 mg/100 ml]). According to one more preferred embodiment, the quantity of Lipiodol is between 50% and 70% mass/volume (thus with respect to the total volume of the preparation). According to one absolutely preferred embodiment, the quantity of Lipiodol is between 62% and 68% mass/volume (thus with respect to the total volume of the preparation).

According to one absolutely preferred embodiment, the pharmaceutical composition according to the invention comprises between 0.004% and 0.2% by mass of Idarubicin, between 0.38% and 2.25% by mass of hydroxyethyl starch, between 50% and 70% by mass of Lipiodol and water for injection (or physiological saline) in a quantity sufficient (q.s.) for 100%.

The present invention also relates to the use of a pharmaceutical composition according to the invention for preparing a medicinal product.

The present invention also relates to the use of a pharmaceutical composition according to the invention for preparing a medicinal product for treating cancer.

The present invention also relates to the use of a pharmaceutical composition according to the invention for preparing a medicinal product for treating primary liver cancer.

The present invention also relates to a method for preparing a composition according to the invention comprising a step consisting of contacting Lipiodol, a molecule with anti-tumour activity and a hydroxyethyl starch.

The present invention also relates to a method for preparing a composition according to the invention comprising a step consisting of contacting Lipiodol and Idarubicin.

DESCRIPTION OF THE EMBODIMENTS

Example 1

The module with anti-tumour activity (Idarubicin, Zavedos®, Pfizer) is prepared to obtain a 5 ml solution (2 mg/ml by simply adding water for injection to the Idarubicin powder), placed in a 30 ml syringe.

Three ml of 130,000 hydroxyethyl starch (0.06 g/ml Voluven®, Fresenius Kabi) is added into this syringe, for a total of 8 ml.

Ten ml of Lipiodol (Lipiodol Ultra Fluide®, Guerbet) is taken up into a further 20 ml syringe.

Mixing is then carried out by transferring the contents of the syringe containing Idarubicin+Voluven quickly into the syringe of Lipiodol using a 3-way valve, so as to obtain a "water-in-oil" type emulsion (the chemotherapy represents the aqueous part, Lipiodol represents the oil-based part). Some fifteen successive transfers are then carried out from one syringe to another, again via the 3-way valve.

The product is then ready to be injected by the hepatic intra-arterial route for treating primary liver cancer.

The experimental results obtained display superior stability of the emulsion using this dose of hydroxyethyl starch, i.e. the emulsion remains stable over time and is subject to very little or no phase separation.

Moreover, it is also possible to obtain with this type of emulsion an increase in fluidity which represents an advantage for transferring into microcatheters.

Intra-arterial injection of this emulsion generates less desaturation in patients, indicating less pulmonary passage of the product. Finally, the scans conducted after the treatment show superior lipiodol impregnation of the liver and tumour nodules.

Example 2

The composition was prepared by mixing an equal volume of Lipiodol and a 1 mg/ml Idarubicin solution. Said mixing was performed as per the protocol described above. The stability of the composition obtained was measured after incubation at 37° C. for 30 min. At this stage, it is observed that 95% of the composition is still in the form of an emulsion. The Idarubicin/Lipiodol micelles are between 20 and 100 µm in size.

These results should be compared to those obtained by Favoulet et al. (Anticancer Drugs. 2001 November; 12(10): 801-6) demonstrating that the Lipiodol/Doxorubicin emulsions are subject to complete phase separation 20 minutes after the preparation thereof.

Three patients were treated with a Lipiodol (10 ml)+ Idarubicin (10 mg) emulsion. The systemic passage of Idarubicin was analysed. The results obtained are as follows:

Cmax Idarubicin=12.5+/−4.8 ng/ml

AUC Idarubicin=61.6+/−23.7 ng·h/ml

These results can be compared to the data published with the Lipiodol/Doxorubicin emulsion (Varela et al., J Hepatol. 2007 March; 46(3):474-81.). This study demonstrated a Cmax of 896 ng/ml, given that the dose of Doxorubicin injected was 70 mg. Therefore, 10 times less Idarubicin is detected in venous blood (12.5 ng/ml) in the Lipiodol-Idarubicin patients. This proves indubitably that the emulsion composition according to the invention is suitable for enhancing the pharmacokinetics of Idarubicin considerably.

The invention claimed is:

1. A Pharmaceutical composition comprising:
   An emulsion of Lipiodol with a molecule with anti-tumour activity and hydroxyethyl starch.

2. The Pharmaceutical composition according to claim 1, wherein said molecule with anti-tumour activity is selected from the group consisting of antimetabolites, alkylating agents, topoisomerase inhibitors, anti-tumour antibiotics and mitotic spindle poisons.

3. The Pharmaceutical composition according to claim 2, wherein said anti-tumour molecule is an intercalating agent, topoisomerase inhibitor.

4. The Pharmaceutical composition according to claim 3, wherein said intercalating agent, topoisomerase inhibitor is an anthracycline.

5. The Pharmaceutical composition according to claim 4, said anthracycline is Idarubicin.

6. The Pharmaceutical composition according to claim 1, wherein said hydroxyethyl starch has a molecular weight between 100,000 and 250,000 Dalton.

7. The Pharmaceutical composition according to claim 6, wherein said hydroxyethyl starch has a molecular weight between 120,000 and 140,000 Dalton.

8. The Pharmaceutical composition according to claim 1, wherein said hydroxyethyl starch has a molar substitution ratio between 0.30 and 0.70.

9. The Pharmaceutical composition according to claim 8, wherein said hydroxyethyl starch has a molar substitution ratio between 0.35 and 0.45.

10. Pharmaceutical composition according to claim 1, wherein said Lipiodol is Lipiodol Ultra-Fluide.

11. The Pharmaceutical composition according to claim 1, wherein the amount of said molecule with anti-tumour activity is between 0.004% and 0.2% (mass/volume) with respect to the total volume of the preparation.

12. The Pharmaceutical composition according to claim 1, wherein the amount of hydroxyethyl starch is between 0.38% and 2.25% (mass/volume) with respect to the total volume of the preparation.

13. The Pharmaceutical composition according to claim 1, wherein the amount of Lipiodol is between 50% and 70% (mass/volume) with respect to the total volume of the preparation.

14. A method for preparing the composition according to claim 1, comprising the step of contacting Lipiodol, the molecule with antitumor activity and hydroxyethyl starch.

15. The pharmaceutical composition according to claim 11, wherein the amount of lipiodol is between 50% and 70% (mass/volume) and the amount of hydroxyethyl starch is between 0.38% and 2.25% (mass/volume).

* * * * *